United States Patent [19]

Swor

[11] Patent Number: 5,385,569
[45] Date of Patent: Jan. 31, 1995

[54] SURGICAL SUTURING ACCESSORY

[75] Inventor: G. Michael Swor, Sarasota, Fla.

[73] Assignee: Surgical Safety Products, Inc., Sarasota, Fla.

[21] Appl. No.: 67,038

[22] Filed: May 21, 1993

[51] Int. Cl.6 .............................. A61B 17/04
[52] U.S. Cl. ............................ 606/148; 606/1; 451/526; 451/539
[58] Field of Search ............... 606/146, 148, 222-232, 606/138, 1; 128/757, 756; 51/262 A, 211 R, 214, 391, 394, 407

[56] References Cited

U.S. PATENT DOCUMENTS

| | | | |
|---|---|---|---|
| 3,819,039 | 6/1974 | Erickson | 606/148 X |
| 3,902,510 | 9/1975 | Roth | 606/146 X |
| 3,945,372 | 3/1976 | Milan et al. | 128/757 |
| 4,069,825 | 1/1978 | Akiyama | 606/158 |
| 4,478,221 | 10/1984 | Heiss | 606/145 |
| 4,969,893 | 11/1990 | Swor | 606/232 |
| 5,016,401 | 5/1991 | Mangus | 51/394 |

Primary Examiner—Peter A. Aschenbrenner
Attorney, Agent, or Firm—Allen, Dyer, Doppelt, Eranjola & Milbrath

[57] ABSTRACT

A surgical accessory is provided for temporarily parking a suture needle, for cleaning a cautery tip, and for cutting suture thread, for which a suture cutting assembly is disclosed that comprises a molded plastic structure with one notched end in which are situated at least one suture holder, to reversibly grasp suture thread guided into the notch, and a suture cutting blade to cut the suture thread. A second embodiment is disclosed comprising an accessory for temporarily parking a suture needle and for cleaning a cautery tip. In yet another embodiment, a flexible arm that can be clamped to a fixed surface is used to support the surgical suturing accessory.

10 Claims, 2 Drawing Sheets

SURGICAL SUTURING ACCESSORY

BACKGROUND OF THE INVENTION

1. Field of the Invention

This invention relates to a surgical accessory for temporarily parking a suture needle, for cutting suture thread after the suture is formed, for holding one end of the cut suture thread, and for cleaning a cautery tip.

2. Description of Related Art

A suture is formed by passing a needle having thread attached thereto through adjacent edges of a wound or incision and then forming a knot in the thread while the edges are held together. The thread is then cut to separate the needle. It is common practice for the surgeon to rest the needle on his/her wrist or the back of his/her hand to change hand positions or while tying the knot. Occasionally, the surgeon is inadvertently pricked while doing this, presenting the possibility of infection. There is a need, consequently, for a safe place to put the needle temporarily while keeping it near at hand. Moreover, resorting to a scissors to cut the suture thread is time consuming, suggesting the need for a more readily available cutting device. In addition, a pad for cleaning cautery tips is often needed and usually requires extra steps to obtain and use.

U.S. Pat. No. 4,069,825, Akiyama, entitled "Surgical Thread and Cutting Apparatus for the Same," discloses a thread for ligating blood vessels and a trigger operated cutter.

U.S. Pat. No. 4,452,246, Bader et al., entitled "Surgical Instrument," discloses a needle holder for suturing which also includes scissor blades to cut the suture thread.

U.S. Pat. No. 4,478,221, Heiss, entitled "Instrument for Use in Surgery," discloses a clamp for retaining a needle and thread and also includes cutting means.

My earlier U.S. Pat. No. 4,969,893, entitled "Disposable Suture Cutter and Needle Holder," discloses a combination surgical cutting blade and foam needle holder.

SUMMARY OF THE INVENTION

The present invention is an accessory for surgical suturing that combines a scratch pad for cleaning a cautery tip and a needle holder for temporary parking of suture needles, with an adhesive layer for mounting in a convenient place in the surgical field, such as the back of a surgeon's nondominant hand. In a preferred arrangement, a surgical suturing accessory comprises a flexible supporting layer having a top and bottom surface with an adhesive material on the bottom surface. An abrasive material layer is disposed on the top surface and has sufficient abrasiveness to clean tissue from cautery tips. In this arrangement, there is provided a cutting assembly formed of a base and a top portion each of which have an elliptical end and spaced at the elliptical end to form a notch. Suture holders are positioned on opposite sides of the notch, and are spaced from a suture cutting blade fixed in the center of the notch so that when suture thread is passed into the notch, the suture thread is cut by the blade. In accordance with this preferred embodiment, the top portion of the suture cutting assembly includes a recess into which is fitted a foam needle holder which serves as a sterile and safe location for inserting a suture needle during operations.

In one specific arrangement, the suture cutting accessory is also provided with means which enables a surgeon to keep his/her nondominant hand free while placing the suture needle tip into the incision, parking the needle, regrasping the needle, etc., until the incision is closed. Still using the dominant hand, the suture thread is drawn through a notch in the suture cutting assembly, where the thread is grasped in a suture holder at one point and cut by a suture cutting blade at another. The suture thread remains in the suture holder until needed again, and is within convenient reach of the surgeon.

In other embodiments, these accessories are affixed to a flexible arm that may be clamped to an operating table, also permitting easy access.

The benefits of these accessories reside in their safety and efficiency features: The chance of needle stick injury is greatly reduced, since manual needle adjustment is eliminated; sterile field contamination caused b needle-glove breaks are avoided; one-handed suturing is possible, freeing the nondominant hand; and suturing time is reduced.

In accordance with these and other objects, the present invention is described in the following with reference to the accompanying drawings.

DETAILED DESCRIPTION OF THE PREFERRED EMBODIMENTS

Figure 1:
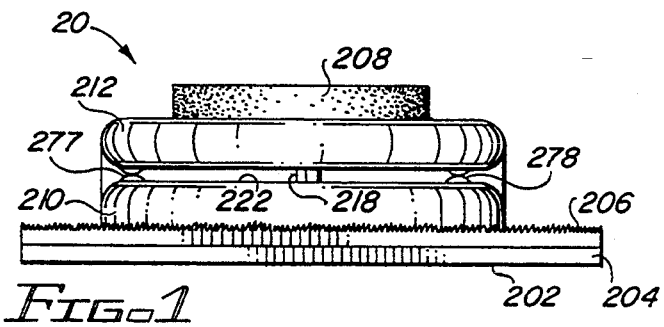
FIG. 1 is a front view of one embodiment of a surgical suturing accessory in accordance with the present invention.
Figure 2:
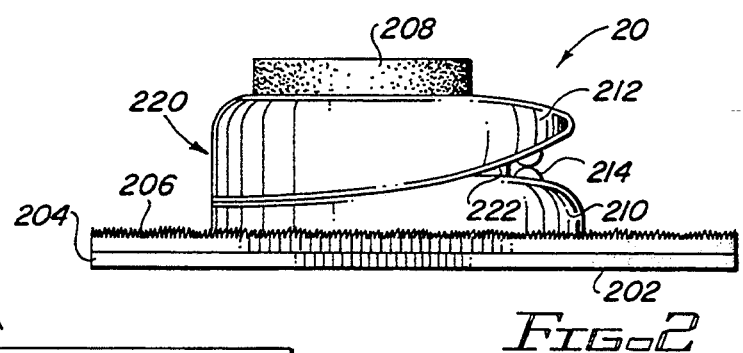
FIG. 2 is a top view of the surgical suturing accessory of FIG. 1.
Figure 3:
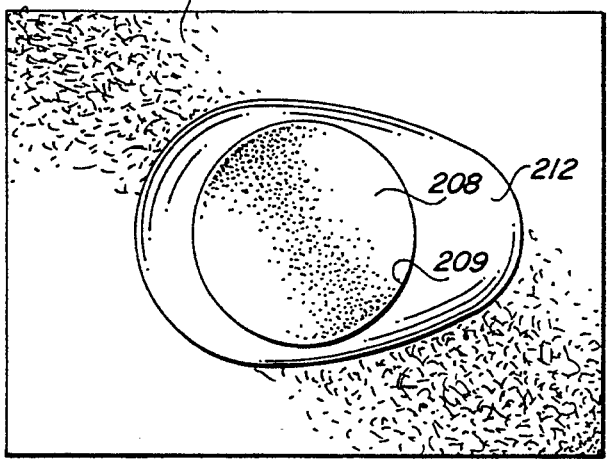
FIG. 3 is a side view of the surgical suturing accessory of FIG. 1.

A detailed description of the preferred embodiments of the present invention will be presented with reference to FIGS. 1-9.

FIGS. 1-6 depict one embodiment of a surgical suturing accessory, in which surgical suturing accessory 20 comprises flexible supporting layer 204, preferably made of a dense foam, with an adhesive material 202 on its bottom surface and scratch pad material 206 affixed on top. In use during surgery, adhesive material 202 is used to attach the surgical suturing accessory 20 to a convenient area, such as the nondominant hand of a surgeon. The scratch pad 206 serves an abrasive material for cleaning tissue from a cautery tip after use. In addition, the accessory 20 suture cutting assembly 220 affixed atop scratch pad 206, and which is composed of a substantially rigid plastic elliptical base 210 glued to a substantially rigid plastic elliptical top portion 212. Both plastic portions have a taper at one end, each tapering inwardly toward the area at which they join, thus forming a notch 222. In the notch 222 are positioned suture holders 277 and 278, and which are attached to the top and/or base portions 212, 210. Suture cutting blade 218 is affixed into the center of notch 222, spaced from suture holders 277 and 278 so that, when suture thread is passed into notch 222, the suture thread is caught between metal portions 214 and 215 of suture holder 277 or 278 and passed across suture cutting blade 218 with sufficient pressure to cut the suture thread. Affixed atop suture cutting assembly is a needle holder 208 formed of a foam plastic body fitted in a recess 209 of the top 212, and which serves as a sterile and safe location for temporarily parking suture needles during suturing operations, since the point of a suture needle may be easily inserted into the needle holder 208.

Figure 5:
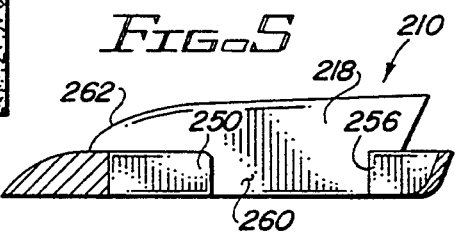
FIG. 5 is a side view of the base of the surgical cutting accessory of FIG. 4.
Figure 4:
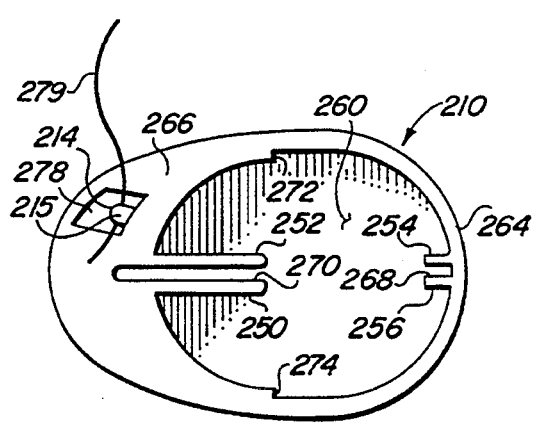
FIG. 4 is a top view of the base of the surgical cutting accessory of FIG. 1.

The interior of the suture cutting assembly will be described with reference to FIGS. 4–6. Base 210, as shown in top view in FIG. 4, comprises a unitary molded plastic structure having a recess 260 defined by rear wall 264 and front wall 266, meeting at shoulders 272 and 274. Projecting from rear wall 264 are two protrusions 254 and 256, which together form a first slot 268. Projecting from front wall 266 are two protrusions 252 and 250, which together form a second slot 270. Slots 268 and 270 are dimensioned to hold suture cutting blade 218, as shown in side view in FIG. 5. The suture cutting blade 218 of the present embodiment comprises a scalpel blade with sharp edge 262. Also illustrated in FIG. 4 is suture holder 278, which comprises a metal flat portion 214 having a curved portion 215 cut out and bent to separate it from flat portion 214 to a dimension suitable for holding suture material 279 firmly.

Figure 6:
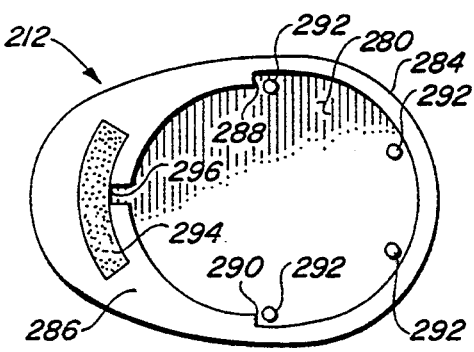
FIG. 6 is a bottom view of the top portion of the surgical cutting accessory of FIG. 4.

Top portion 212, as shown in bottom view in FIG. 6, comprises a unitary molded plastic structure having a recess 280 defined by rear wall 284 and front wall 286, meeting at shoulders 288 and 290. Four cylindrical protrusions 292 extend beyond the height of walls 284 and 286. Recess 294 in front wall 286 is filled with a flexible material 296. When assembled, protrusions 292 secure top portion 212 to bottom portion 210, with bottom portion shoulders 272 and 274 serving to provide a location for the two protrusions 292 situated behind top portion shoulders 288 and 290. Blade 218 is affixed as shown in FIG. 5, and, upon joining top 212 and bottom 210 portions, blade 218 fits into slot 296 in wall 286 and flexible material 294 and is thus kept from deflection.

Figure 7:
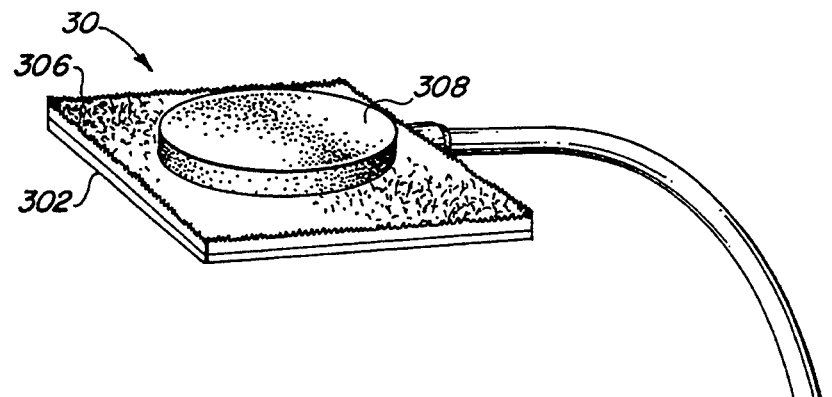
FIG. 7 is a side view of another embodiment of a surgical suturing accessory in accordance with the present invention.
Figure 7:
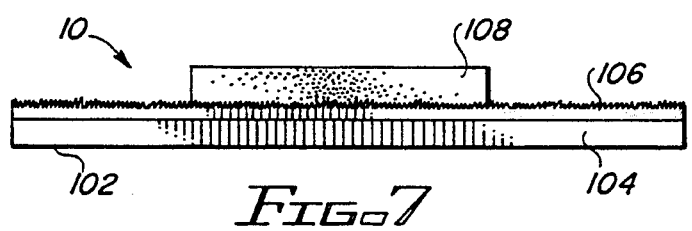
Figure 8:
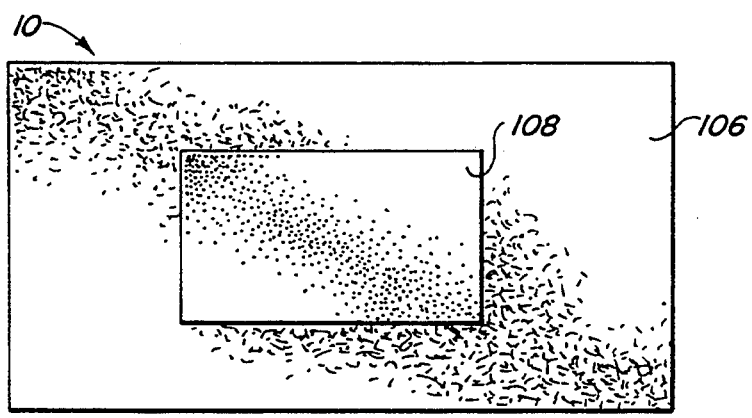
FIG. 8 is a top view of the surgical suturing accessory of FIG. 7.

FIGS. 7 and 8 illustrate another embodiment of a disposable surgical suturing accessory 10, indicating a rectangular layered structure. The flexible supporting layer 104, made of foam, has an adhesive material 102 on its bottom surface. On the top surface of flexible supporting layer 104 is affixed a scratch pad material 106. Attached to the top of the scratch pad material 106 is needle holder 108, made of a foam material into which suture needles may be readily inserted. The spatial extent of the needle holder 108 is smaller than that of the scratch pad material 106, in order to leave sufficient scratch pad area for use in cleaning cautery tips.

In use during surgery, adhesive material 102 is used to attach the surgical suturing accessory 10 to a convenient area, such as discussed for accessory 20. The scratch pad 106 functions as has already been mentioned. Needle holder 108 serves as a sterile and safe location for temporarily parking suture needles during suturing operations, since the point of a suture needle may be easily inserted into the needle holder 108, but the point will neither penetrate through scratch pad 106 into flexible support layer 104 nor beyond, into the surgeon's hand.

Figure 9:
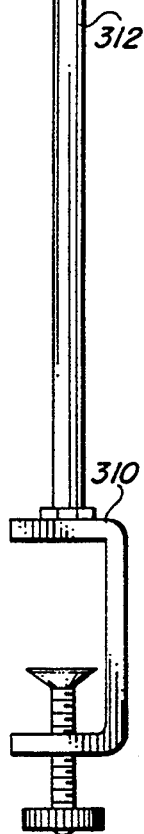
FIG. 9 is a side view of a third embodiment of a surgical suturing accessory.

FIG. 9 illustrates yet another embodiment of surgical suturing accessory 30, this apparatus capable of being detachably affixed to a surface, such as an operating table, with clamp 310. Flexible arm 312 serves to position surgical suturing accessory 30, which comprises rigid base 302, scratch pad 306, and needle holder 308.

It is to be understood that these embodiments are representative of possible variations of the invention disclosed herein, and that those skilled in the art will recognize other potential embodiments within the scope of the invention.

What is claimed is:

1. A surgical suturing accessory for use with suture needles and cautery tips, comprising:
    a flexible supporting layer having a top surface and a bottom surface;
    an adhesive material affixed to the bottom surface of the flexible supporting layer;
    an abrasive material layer sufficiently abrasive to clean tissue from cautery tips, the abrasive material affixed to the top of the flexible supporting layer; and
    a needle holder carried by the abrasive material layer and dimensioned smaller than the abrasive layer so as to leave exposed sufficient abrasive material for permitting the abrading of a cautery tip, the needle holder formed of soft material into which a suture needle may be readily placed and removed.

2. The surgical suturing accessory recited in claim 1, wherein the flexible supporting layer and adhesive material comprise adhesive-backed foam.

3. The surgical suturing accessory recited in claim 1, wherein the abrasive material comprises a scratch pad.

4. The surgical suturing accessory recited in claim 1, wherein the needle holder comprises a foam plastic.

5. A surgical suturing accessory for use with a cautery tips and a suture needle having suture material thereon, comprising:
    a flexible supporting layer having a top surface and a bottom surface;
    an adhesive material affixed to the bottom surface of the flexible supporting layer;
    an abrasive material layer sufficiently abrasive to clean tissue from cautery tips and affixed to the top of the flexible supporting layer;
    a suture cutting assembly affixed to the abrasive material layer, dimensioned smaller than the abrasive material layer so as to leave exposed sufficient abrasive material for abrading a cautery tip.

6. The suture accessory of claim 5, wherein the suture cutting assembly comprises:
    a substantially elliptical base tapering inwardly at one end;
    a substantially elliptical top portion affixed to the base, tapering at the same end as that of the base, said tapers forming a notch;
    a suture holder affixed in at least one side of the notch of the suture cutting assembly;
    a cutting blade affixed substantially in the center of the notch of the suture cutting assembly;
    the suture holder and cutting blade positioned so suture material may be brought into contact with the suture holder and the cutting blade with sufficient force to cut the suture thread, one cut end of the suture material remaining in the suture holder after the cutting operation.

7. The suture accessory of Claim 5, further comprising:
   a needle holder affixed to the top portion of the suture cutting assembly, the needle holder formed of soft material, into which a suture needle may be readily placed and from which the suture needle may be readily removed.

8. The surgical suturing accessory recited in claim 5, wherein the flexible supporting layer and adhesive material comprise adhesive-backed foam.

9. The surgical suturing accessory recited in claim 5, wherein the abrasive material comprises a scratch pad.

10. The surgical suturing accessory recited in claim 7, wherein the needle holder comprises foamed plastic.

* * * * *